United States Patent
Jirkovsky et al.

[11] Patent Number: 5,118,675
[45] Date of Patent: Jun. 2, 1992

[54] QUINOXALINE PHOSPHONO-AMINO ACIDS

[75] Inventors: Ivo L. Jirkovsky, Plainsboro, N.J.; Reinhardt B. Baudy, Yardley, Pa.; Lynne P. Greenblatt, Lambertville, N.J.

[73] Assignee: American Home Products Corporation, New York, N.Y.

[21] Appl. No.: 656,894

[22] Filed: Feb. 15, 1991

[51] Int. Cl.$^5$ .................. A61K 31/675; C07F 9/6509
[52] U.S. Cl. ....................................... 514/80; 544/337
[58] Field of Search ........................... 544/337; 514/80

[56] References Cited
U.S. PATENT DOCUMENTS

| | | | |
|---|---|---|---|
| 4,657,899 | 4/1987 | Rzeszotarski et al. | 514/120 |
| 4,746,653 | 5/1988 | Hutchison et al. | 514/89 |
| 4,888,347 | 12/1989 | Woodruff et al. | 514/289 |

Primary Examiner—Mukund J. Shah
Assistant Examiner—E. Bernhardt
Attorney, Agent, or Firm—Richard K. Jackson

[57] ABSTRACT

The compounds of the formula:

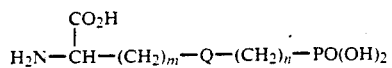

in which Q is the quinoxaline nucleus; m is one of the integers 0, 1 or 2; n is one of the integers 1, 2 or 3; or a pharmaceutically acceptable salt, alkyl ester or

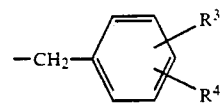

where $R^3$ and $R^4$ are, independently, hydrogen, nitro, halo or methoxy, are NMDA antagonists useful in the treatment and prevention of central nervous system related pathological conditions resulting from overstimulation by excitatory amino acids.

15 Claims, No Drawings

QUINOXALINE PHOSPHONO-AMINO ACIDS

BACKGROUND OF THE INVENTION

L-Glutamate and L-aspartate, the endogenous acidic amino acids, have been firmly established as major excitatory neurotransmitters. The action of these excitatory amino acids is mediated by several distinct receptor subtypes of which the best studied one is the N-methyl-D-aspartate (NMDA) receptor. Excessive activation of the NMDA receptor complex may cause neuronal overstimulation with pathological consequences. Experimental evidence suggests that a prolonged, agonist-evoked conductance of the NMDA-gated ion channel permits an abnormal enhancement of calcium entry, and the resulting increased levels of intracellular calcium play a pivotal, deleterious role in the excitotoxic neuronal damage, neurodegeneration, and delayed neuronal death.

Excitatory amino acids have been implicated in neuropathologies of traumatic, endogenous-genetic, and environmental origin. Brain damage associated with anoxia, hypoglycemia, traumatic injury, stroke, epilepsy, specific metabolic defects, and some chronic neurodegenerative diseases is, to a large extent, produced by excitotoxic mechanisms.

A number of studies have demonstrated that blockade of the NMDA-subclass receptor significantly reduces neuronal damage and loss which occurs in animal models mimicking a variety of neuropathological situations. These observations strongly indicate that NMDA antagonists offer effective neuroprotection in several clinical settings. Thus, agents antagonizing the excitotoxic effects mediated by the NMDA receptor are beneficial in the treatment of ischaemic conditions, stroke, brain or spinal cord injury, and generally, in patients with escalating levels of excitatory neurotransmitters. Specific applications also include therapy of senile dementia Alzheimer-type, parkinsonian dementia complex, Huntington's chorea, and other dominant or recessive spinocerebellar degenerations where NMDA antagonists prevent or retard the progression of the disease.

DESCRIPTION OF THE INVENTION

In accordance with this invention, there is provided a group of novel NMDA antagonists, pharmaceutical compositions containing them and a method for using the antagonists to prevent and/or relieve the physiological effects induced by overstimulation of excitatory amino acid receptors of the central nervous system. The NMDA antagonists of this invention are embraced by the following structural formula:

$$\begin{array}{c} CO_2H \\ | \\ H_2N-CH-(CH_2)_m-Q-(CH_2)_n-PO(OH)_2 \end{array}$$

in which
Q is the quinoxaline nucleus;
m is one of the integers 0, 1 or 2;
n is one of the integers 1, 2 or 3;
or a pharmaceutically acceptable salt, alkyl ester, in which the alkyl group contains from 1 to 6 carbon atoms, or

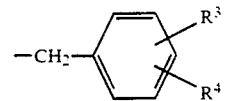

where $R^3$ and $R^4$ are, independently, hydrogen, nitro, halo or methoxy.

The more preferred compounds of this invention are of the formula:

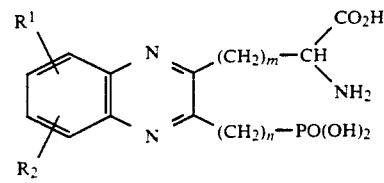

in which
$R^1$ and $R^2$ are, independently, hydrogen, alkyl of 1 to 6 carbon atoms, alkoxy of 1 to 6 carbon atoms, or halo, or taken together, $R^1$ and $R^2$ are butadienylene; or a pharmaceutically acceptable salt, alkyl ester, in which the alkyl group contains 1 to 6 carbon atoms, or benzyl ester thereof.

Of these compounds, when $R^1$ or $R^2$ is an alkyl substituent, it preferably contains 1 to 4 carbon atoms, when a halogen is preferably chlorine, bromine or fluorine, m is 1 and n is 1.

The pharmaceutically acceptable salts are the alkali metal salts (sodium or potassium), the alkaline earth metal salts (calcium or magnesium) and ammonium salts. Mono-, di or triesters of the carboxylic acid and phosphonic acid substituents include the alkyl esters (methyl, ethyl, propyl, isopropyl, butyl, tert-butyl, pentyl, hexyl and the like) and less preferably the benzyl or substituted benzyl esters (paranitrobenzyl, parachlorobenzyl, 2,4-dimethoxybenzyl, and the like).

The compounds of this invention contain an asymmetric carbon atom and therefore appear as racemic mixtures which are readily resolved into their pure enantiomers by conventional means.

The compounds of this invention are prepared by reaction of a bis(haloalkyl)quinoxaline with a trialkyl phosphite under Michaelis-Arbuzov reaction conditions to obtain a dialkyl (haloalkyl)quinoxaline-alkylphosphonate which is then used to C-alkylate an N-benzylidene glycine ester in the presence of an alkali metal alkoxide. Alternatively, alkylation may be accomplished with dialkyl acetamidomalonate and an alkali metal alkoxide. Acidic hydrolysis of either intermediate provides the free acids. Where the intermediate is derived from an N-benzylidene glycine ester, a step-wise hydrolysis may be employed, first removing the benzylidene group, then dialkylating the phosphonate ester with trimethylsilyl bromide, and finally employing basic hydrolysis or hydrogenolysis of the carboxylate ester. The order of these steps may be changed as desired.

The requisite 2,3-bis(bromomethyl)quinoxaline is commercially available. Substituted and unsubstituted bis(haloalkyl)quinoxaline derivatives are prepared by the method of Wegman et al., Helvet. Chim. Acta 29, 101 (1946). The substituted orthophenylenediamine reactants are obtained by reduction of substituted orthodinitrobenzenes or substituted nitroanilines employing $SnCl_2$/HCl (Org. Synth. Coll. Vol. II, p. 130), catalytic hydrogenation (Org. Synth. Coll. Vol. V., p. 829), Raney Ni/$N_2H_4$ (Can. J. Chem. 38, 2363, 1960), or $(NH_4)_2S$ in ethanol (J. Chem. Soc. 87, 1269, 1905). Ortho-dinitration of substituted benzenes is conducted conventionally.

The following examples illustrate the preparation of representative compounds of the invention.

EXAMPLE 1

α-Amino-3-(phosphonomethyl)-2-quinoxaline-propanoic Acid

A mixture of 1,2-phenylenediamine (0.1 mole, 10.8 g) and 1,4-dibromo-2,3-butanedione (0.1 mole, 24.4 g) was refluxed in benzene (200 mL) using a Dean-Stark trap for one hour. The reaction mixture was then evaporated to dryness in vacuo and the residue flash chromatographed on silica gel (15:1). Elution with 15% hexane/chloroform afforded 29.38 g of 2,3-bis(bromomethyl)-quinoxaline, m.p. 150°-151° C.; $^1$H NMR ($CDCl_3$, 200 MHz): δ4.92 (s, 4H, $CH_2$), 7.8 (m, 2H, ArH), 8.05 (m, 2H, ArH).

A mixture of 2,3-bis(bromomethyl)quinoxaline (15.8 mmole, 5 g) and trimethyl phosphite (15.8 mmole, 1.96 g) was refluxed in toluene (200 mL) for 6 hours. The reaction mixture was then evaporated in vacuo to dryness and the residue flash chromatographed on silica gel (40:1). Elution with ethyl acetate afforded 2.36 g of dimethyl 3-bromomethyl-quinoxaline-2-methylphosphonate, m.p. 99°-102° C.; $^1$H NMR ($CDCl_3$, 200 MHz): δ3.73 (s, 3H, $OCH_3$), 3.79 (s, 3H, $OCH_3$), 3.85 (d, J=21.7 Hz, 2H, $CH_2$—P), 4.98 (s, 2H, $CH_2$), 7.74 (m, 2H, ArH), 8.02 (m, 2H, ArH).

A solution of N-benzylidene glycine ethyl ester (17.7 mmole, 3.4 g) in dry THF (30 mL) was added dropwise to a solution of potassium t-butoxide (17.7 mmole, 1.98 g) in dry THF (50 mL) at −78° C. under nitrogen. The resulting mixture was stirred for 2 minutes, and then dimethyl 3-bromomethyl-quinoxaline-2-methylphosphonate (17.7 mmole, 6.1 g) in dry THF (60 mL) was added dropwise, and stirring was continued at −78° C. for 60 minutes. The reaction mixture was allowed to warm to room temperature in the course of 4 hours, it was poured into ice-cold brine (150 mL) and extracted with ethyl acetate (3×100 mL). The combined extracts were washed with brine, dried over magnesium sulfate, filtered, and concentrated in vacuo. A rapid purification by flash chromatography (silica gel 50:1, ethyl acetate) afforded N-benzylidene α-amino-3-[(dimethoxyphosphinyl)methyl]-2-quinoxalinepropanoic acid ethyl ester; MS (pos. FAB) 456 (MH$^+$); $^1$H NMR (DMSO-$d_6$, 400 MHz): δ8.54 (s, 1H, CH=N).

An alternative flash chromatography (silica gel 40:1, elution with 2-5% methanol in chloroform) removed the benzylidene group, and α-amino-3-[(dimethoxyphosphinyl)methyl]-2-quinoxalinepropanoic acid ethyl ester was obtained in 85% yield (5.5 g). $^1$H NMR ($CDCl_3$, 200 MHz): δ1.22 (t, J=7.8 Hz, 3H, $CH_3$), 3.55 (m, 2H, $CH_2$), 3.7 (d, J=20.3 Hz, 2H, $CH_2$—P), 3.75 and 3.78 (singlets, 6H, $OCH_3$), 4.15 (m, 3H, $CH_2$ of ethyl and CH), 7.7 (m, 2H, ArH), 7.98 (m, 2H, ArH).

A solution of the N-benzylidene α-amino-3-[(dimethoxyphosphinyl)methyl]-2-quinoxalinepropanoic acid ethyl ester (1.6 mmole, 740 mg, prepared above) in methylene chloride (20 mL) was treated with trimethylsilyl bromide (13 mmole, 1.7 mL). The reaction mixture was refluxed for 4 hours, and evaporated to dryness in vacuo. The residue was shaken with water (20 mL) for 5 min, and then washed with diethyl ether (20 mL). The aqueous layer was separated, filtered, and evaporated in vacuo. The crude product (hydrobromide) was stripped with benzene, dissolved in ethanol (10 mL), and propylene oxide (4 mL) was added at once. This mixture was stirred at room temperature for 30 minutes, evaporated, and the residual material was triturated with ethanol, acetonitrile, and diethyl ether to precipitate α-amino-3-(phosphonomethyl)-2-quinoxalinepropanoic acid ethyl ester. Recrystallization from ethanol-diethyl ether gave 450 mg of crystals, m.p. 169°-172° C. (dec); MS (neg. FAB) 338. $^1$H NMR ($D_2O$, 400 MHz): δ0.96 (t, J=7 Hz, 3H, $CH_3$), 3.34 (m, 2H, $CH_2$—P), 3.86 (dd, $J_1$=13.7 Hz, $J_2$=4.2 Hz, 2H, $\underline{CH_2}$—CH), 4.12 (q, J=7 Hz, 2H, $CH_2$ of ethyl), 4.27 (m, 1H, CH), 7.67 (m, 2H, H-6 and H-7), 7.86 (d, J=8 Hz, 2H, H-5 and H-8).

The crude hydrobromide of α-amino-3-(phosphonomethyl)-2-quinoxalinepropanoic acid ethyl ester (1.4 mmole, 600 mg) was added to 1N aqueous potassium hydroxide (5.75 mL). The mixture was stirred overnight at room temperature, and then applied to an ion-exchange column (20 mL volume, Amberlite IRA 400) which had been prewashed with deionized water (40 mL). The column was washed to neutrality with deionized water, and the elution was continued with 0.5N hydrochloric acid. The acidic eluate was evaporated to dryness under reduced pressure, the residue was stripped with water (2×30 mL), benzene (2×30 mL), and dissolved in ethanol (10 mL). This solution was treated with propylene oxide (14.5 mmole, 1 mL), stirred for 30 minutes, the precipitate was collected by filtration, washed successively with cold ethanol and diethyl ether, and dried in vacuo at 85° C. The α-amino-3-(phosphonomethyl)-2-quinoxalinepropanoic acid (300 mg) melted at 176° C. with decomposition; MS (pos. FAB) 312 (MH$^+$); $^1$H NMR ($D_2O$, 400 MHz): δ3.29 (dd, $J_1$=21 Hz, $J_2$=6 Hz, 2H, $CH_2$—P), 3.69 (m, 2H, $CH_2$), 4.41 (m, 1H, CH), 7.56 (m, 2H, ArH), 7.71 and 7.81 (m, 2H, ArH).

Elemental analysis for $C_{12}H_{14}N_3O_5P \cdot 2H_2O$: Calc'd: C, 41.50; H, 5.19, N, 12.10. Found: C, 41.80; H, 4.62; N, 11.62.

EXAMPLE 2

α-Amino-3-(phosphonomethyl)-2-quinoxaline-propanoic Acid by Direct Hydrolysis

A solution of α-amino-3-8 (dimethoxyphosphinyl)methyl]-2-quinoxalinepropanoic acid ethyl ester (11.7 mmole, 4.3 g) in 6N hydrochloric acid (25 mL) was refluxed for 3 hours, charcoaled at 80° C., and filtered through Celite ®. The filtrate was washed with diethyl ether and evaporated to dryness in vacuo. The residue was stripped with water (50 mL), benzene (3×50 mL), dissolved in ethanol (75 mL), and propylene oxide (8.4 mL) was added at once. The resulting mixture was kept at ambient temperature for 30 minutes, the precipitate was collected by filtration, washed with diethyl ether, and dried in vacuo at 85° C. The product (2.4 g) melted at 178° C. with decomposition; MS (neg. FAB) 310; $^1$H NMR (DMSO-$d_6$, 400 MHz): δ3.56 (m, 2H, $CH_2$—P), 3.8 (d, J=6.7 Hz, 2H, $CH_2$), 4.57 (t, J=6.7 Hz, 1H, CH), 7.79 and 8.0 (m, 4H, ArH).

Elemental Analysis for $C_{12}H_{14}N_3O_5P \cdot 2H_2O$: Calc'd: C, 41.50; H, 5.19; N, 12.10. Found: C, 41.45; H, 4.58; N, 12.01.

EXAMPLE 3

Enantiomers of
α-Amino-3-(phosphonomethyl)-2-quinoxaline-
propanoic Acid

Optical resolution was carried out at the stage of α-amino-3-[(dimethoxyphosphinyl)methyl]-2-quinoxalinepropanoic acid methyl ester. $^1$H NMR (CDCl$_3$, 400 MHz): δ3.55 (m, 2H, CH$_2$), 3.69 (d, J=24 Hz, 2H, CH$_2$—P), 3.73, 3.76, 3.79 (singlets, 9H, OCH$_3$), 4.23 (m, 1H, CH), which was prepared following the procedures of Example 1 but replacing N-benzylidene glycine ethyl ester with the corresponding methyl ester.

A heated solution of the racemic triester (33.7 mmole, 11.9 g) in acetonitrile (100 mL) was treated with a hot solution of (−) dibenzoyl-L-tartaric acid monohydrate (33.7 mmole, 12.7 g) in acetonitrile (60 mL). The resulting solution was allowed to cool overnight, and the crystalline precipitate was collected by filtration. Two crystallizations of this material from acetonitrile afforded 4.9 g of the diastereomeric salt, m.p. 132°-137° C.; [α]D$^{25}$−105° (c, 1.5, ethanol). Enantiomeric purity, 98.5%, was determined by HPLC on a Crownpak column (75 cm×4.6 cm i.d.); mobile phase: 5 parts of isopropanol, 95 parts of water acidified to pH 2 with perchloric acid. Separation of retention times ranged from 50 to 100 seconds. Typically, a flow rate of 0.7 mL/min and column temperature of 10° C. gave a retention time 11.6 minutes for the purified enantiomeric triester while its optical antipode (1.5%) had retention time of 12.7 minutes.

An aqueous solution of the diastereomeric salt was mixed with saturated sodium bicarbonate (40 mL) and the resulting suspension was extracted with methylene chloride (3×40 mL). The combined extracts were dried over magnesium sulfate, filtered, and evaporated to yield 2.02 g of the free, enantiomeric triester as a clear, straw colored oil. Subsequent hydrolysis, according to the procedure of Example 2, furnished 1.06 g of (+)-α-amino-3-(phosphonomethyl)-2-quinoxalinepropanoic acid, m.p. 174° C. with decomposition; [α]D$^{25}$+4.4 (c 1.0, ethanolic HCl). Enantiomeric purity, 98.6%, was determined by HPLC on a 15 cm-Novapak Phenyl column using 0.005M NH$_4$H$_2$PO$_4$/0.005M CuSO$_4$/0.01 ML-proline aqueous solution as a mobile phase. At a flow rate 1 mL/min., the dextrorotatory enantiomer exhibited retention time 9.7 minutes, whereas the levorotatory enantiomer had retention time of 11.4 minutes.

Initial resolution with (−) dibenzoyl-L-tartaric acid provided mother liquors enriched with the salt of the opposite enantiomer of α-amino-3-[(dimethoxyphosphinyl)methyl]-2-quinoxalinepropanoic acid methyl ester. The combined filtrates were evaporated in vacuo, and the residue was partitioned between saturated sodium bicarbonate (150 mL) and methylene chloride (3×150 mL). The organic extracts were dried over magnesium sulfate, filtered, and the solvent was removed on a rotovapor. The residual oil was flash chromatographed on 150 g of silica gel. Elution with 4% methanol in chloroform yielded 4.36 g of the triester (homogenous by TLC; enantiomeric purity 73%). This material (12.3 mmole, 4.36 g) was dissolved in hot acetonitrile (40 mL), and then treated with a hot solution of (+) dibenzoyl-D-tartaric acid (12.3 mmole, 4.42 g) in acetonitrile (20 mL). Diethyl ether (30 mL) was added to the mixture while still warm, the clear solution was allowed to stand at ambient temperature for two days, and the crystalline salt was collected by filtration. Three crystallizations from acetonitrile-diethyl ether (2:1) afforded 1.6 g of the diastereomeric salt, m.p. 129°-133° C.; enantiomeric purity 91%. Further crystallization yielded crystals, m.p. 130°-135° C. with enantiomeric purity 95.5%.

Decomposition of the salt and hydrolysis of the resulting free amino-ester, as described above, yielded 0.37 g of (−)-α-amino-3-(phosphonomethyl)-2-quinoxalinepropanoic acid, m.p. 176° C. with decomposition; [α]D$^{25}$−3.9° (c, 1.0, ethanolic HCl); enantiomeric purity 96.4%.

EXAMPLE 4

α-Amino-6,7-dimethyl-3-(phosphonomethyl)-2-quinoxalinepropanoic Acid

Following the procedure of Example 1 with 2,3-bis(bromomethyl)-6,7-dimethyl-quinoxaline, m.p. 152°-154° C.; $^1$H NMR (DMSO-d$_6$, 400 MHz): δ2.46 (s, 6H, CH$_3$), 4.99 (s, 4H, CH$_2$), 7.84 (s, 2H, ArH), the intermediate dimethyl 3-bromomethyl-6,7-dimethyl-quinoxaline-2-methylphosphonate, m.p. 111°-112° C.; $^1$H NMR (DMSO-d$_6$, 400 MHz): δ2.45 and 2.46 (singlets, 6H, CH$_3$), 3.67 and 3.70 (singlets, 6H, CH$_3$O), 3.82 (d, J=21.9 Hz, 2H, CH$_2$—P), 5.01 (s, 2H, CH$_2$), 7.82 (s, 2H, ArH) was obtained and converted to α-amino-3-[(dimethoxyphosphinyl)methyl]-6,7-dimethyl-2-quinoxalinepropanoic acid ethyl ester; which was partially hydrolyzed to α-amino-6,7-dimethyl-3-(phosphonomethyl)-2-quinoxalinepropanoic acid ethyl ester and with subsequent or simultaneous hydrolysis to α-amino-6,7-dimethyl-3-(phosphonomethyl)-2-quinoxalinepropanoic acid; m.p. 198°-200° C.; $^1$H NMR (DMSO-d$_6$, 1 drop of DCl, 400 MHz): δ2.43 (s, 6H, CH$_3$), 3.36 (m, 2H, CH$_2$—P), 3.75 (m, 2H, CH$_2$), 4.52 (t, J=6 Hz, 1H, CH), 7.76 and 7.79 (singlets, 2H, ArH).

Elemental analysis for C$_{14}$H$_{18}$N$_3$O$_5$P.H$_2$O: Calc'd: C, 47.05; H, 5.64; N, 11.76. Found: C, 47.54; H, 5.82; N, 11.36.

EXAMPLE 5

α-Amino-3-(phosphonomethyl)-2-benzo[g]quinoxaline-propanoic Acid

Following the procedure of Example 1, 1,4-dibromo-2,3-butanedione is condensed with 2,3-diaminonaphthalene to obtain 2,3-bis(bromomethyl)benzo[g]quinoxaline, m.p. 190°-191° C.; $^1$H NMR (DMSO-d$_6$, 400 MHz): δ5.07 (s, 4H, CH$_2$), 7.68 and 8.26 (double doublets, 4H, H-7 and H-8, H-6 and H-9, resp.), 8.78 (s, 2H, H-5 and H-10).

Reaction of the product of the preceding paragraph with trimethyl phosphite produced dimethyl 3-bromomethyl-benzo[g]quinoxaline-2-phosphonate as an oil; $^1$H NMR (DMSO-d$_6$, 400 MHz): δ3.73 and 3.76 (singlets, 6H, CH$_3$O), 3.94 (d, J=22 Hz, 2H, CH$_2$—P), 5.10 (s, 2H, CH$_2$), 7.66 and 8.24 (m, 4H, ArH), 8.74 (s, 2H, H-5 and H-10).

The product of the preceding paragraph is reacted with N-benzylidene glycine benzyl ester and the reaction product is chromatographed (silica gel 40:1, elution with 2-5% methanol in chloroform) to remove the benzylidene group and yield α-amino-3-[(dimethoxyphosphinyl)methyl]2-benzo[g]quinoxalinepropanoic acid benzyl ester which is demethylated with trimethylsilyl bromide to obtain α-amino-3-(phosphonomethyl)-2-benzo[g]quinoxalinepropanoic acid benzyl ester.

Palladium on charcoal (10%, 100 mg) was added to a solution of the benzyl ester (2.3 mmole, 910 mg) in acetic acid (30 mL). The mixture was hydrogenated at normal pressure for 14 hours, diluted with water (40 mL), filtered, and evaporated in vacuo. The residue was then dissolved in 5% ammonium hydroxide (30 mL), the hot solution was charcoaled, and filtered through Celite ®. The filtrate was concentrated, and acetone was added to induce crystallization. After 2 hours at 0° C., ammonium α-amino-3-(phosphonomethyl)-2-benzo[g]quinoxalinepropanoate (600 mg) was collected by filtration, washed with acetone, and recrystallized from water-acetonitrile-acetone; m.p. 215° C.; MS (pos. FAB) 362 (MH+). $^1$H NMR (DMSO-d$_6$, 1 drop of DCl, 400 MHz): δ3.85 (m, 2H, CH$_2$), signal for CH$_2$—P exchangeable with DCl, 4.6 (m, 1H, CH), 7.6 and 8.2 (m, 4H, ArH), 8.62 and 8.66 (singlets, 2H, H-5 and H-10).

Elemental analysis for C$_{16}$H$_{19}$N$_4$O$_5$P.0.25H$_2$O: Calc'd: C, 50.20; H, 5.13; N, 14.64. Found: C, 50.39; H, 5.04; N, 14.30.

EXAMPLE 6

α-Amino-7-(phosphonomethyl)-6-quinoxalinepropanoic Acid

A solution of 6,7-dimethyl-quinoxaline (37.9 mmole, 6 g) in CCl$_4$ (400 mL) was treated at once with N-bromosuccinimide (76 mmole, 13.53 g) in the presence of dibenzoyl peroxide (200 mg). The reaction mixture was refluxed for 4 hours, and then cooled to 0° C. The precipitate was removed by filtration, the filtrate was evaporated, and the residue chromatographed (silica gel, 2% methanol in chloroform) to give 6 g of 6,7-bis(bromomethyl)-quinoxaline. $^1$H NMR (DMSO-d$_6$, 200 MHz): δ5.1 (s, 4H, CH$_2$), 8.28 (s, 2H, H-5 and H-8), 9.0 (s, 2H, H-2 and H-3).

The 6,7-bis(bromomethyl)quinoxaline was reacted with trimethyl phosphite to obtain the intermediate dimethyl phosphonate which was converted to α-amino-7-[(dimethoxyphosphinyl)methyl]-6-quinoxalinepropanoic acid methyl ester using N-benzylidene glycine methyl ester. Hydrolysis with 6N hydrochloric acid afforded α-amino-7-(phosphonomethyl)-6-quinoxalinepropanoic acid; m.p. 250° C.; MS (neg. FAB) 310; $^1$H NMR (DMSO-d$_6$, 1 drop of DCl, 400 MHz): δ3.3-3.6 (overlapping multiplets, 4H, CH$_2$), 4.39 (t, J=6 Hz, 1H, CH), 7.99 (d, J=3.5 Hz, 1H, ArH), 8.03 (s, 1H, ArH), 8.89 (broad s, 2H, H-2 and H-3).

Elemental analysis for C$_{12}$H$_{14}$N$_3$O$_5$P.0.3EtOH: Calc'd: C, 46.56; H, 4.90; N, 12.93. Found: C, 46.37; H, 4.67; N, 12.63.

EXAMPLE 7

α-Amino-6,7-dichloro-3-(phosphonomethyl)-2-quinoxalinepropanoic Acid

Following the procedure of Example 1, condensation of 1,4-dibromo-2,3-butanedione with 1,2-diamino-4,5-dichlorobenzene yielded 2,3-bis(bromomethyl)-6,7-dichloro-quinoxaline, m.p. 154°-156° C.; $^1$H NMR (CDCl$_3$, 200 MHz): δ4.86 (s, 4H, CH$_2$), 8.18 (s, 2H, ArH).

Reaction of the product of the preceding paragraph with trimethyl phosphite produced dimethyl 3-(bromomethyl)-6,7-dichloroquinoxaline-2-methylphosphonate dimethyl 3-bromomethyl-6,7-dichloro-quinoxaline-2-methylphosphonate, m.p. 128°-130° C.; $^1$H NMR (CDCl$_3$, 200 MHz): δ3.74 and 3.80 (singlets, 6H, CH$_3$O), 3.83 (d, J=15 Hz, 2H, CH$_2$—P), 4.93 (s, 2H, CH$_2$), 8.17 (s, 2H, ArH).

A solution of diethyl acetamidomalonate (2.05 mmole, 0.45 g) in ethanol (20 mL) was treated dropwise with a solution of sodium ethoxide (2.05 mmole in 4 mL of ethanol) at 25° C. under dry nitrogen. The mixture was stirred for 15 minutes, a solution of dimethyl 3-bromomethyl-6,7-dichloro-quinoxaline-2-methylphosphonate (2.05 mmole, 0.858 g) in ethanol (20 mL) was added at once, and stirring was continued for 3 hours at ambient temperature. The reaction mixture was concentrated and partitioned between 5% aqueous sodium bicarbonate (50 mL) and ethyl acetate (2×50 mL). The combined organic extracts were dried over magnesium sulfate, filtered and evaporated. The residue was flash chromatographed (silica gel, ethyl acetate with 0-5% methanol) to give 450 mg of acetylamino-[6,7-dichloro-3-[(dimethoxyphosphinyl)methyl]quinoxalin-2-yl]methyl-propanedioic acid diethyl ester; m.p. 130°-132° C.; $^1$H NMR (CDCl$_3$, 200 MHz): δ1.23 (t, J=8.6 Hz, 6H, CH$_3$ of ethyl), 1.88 (s, 3H, CH$_3$CO), 3.64 (d, J=23.3 Hz, 2H, CH$_2$—P), 3.78 and 3.83 (singlets, 6H, CH$_3$O), 4.2-4.35 (overlapping signals, 6H, CH$_2$), 6.97 (s, 1H, NH), 7.98 and 8.13 (singlets, 2H, ArH).

The intermediate acetylamino derivative prepared in the preceding paragraph (24.7 mmole, 13.6 g) was refluxed in 6N hydrochloric acid (136 mL) for 2 hours, the hot solution was charcoaled, and filtered through Celite ® (rinsing the cake with 50 mL of hot water). The filtrate was cooled, washed with diethyl ether, and evaporated in vacuo. The residue was stripped with water (2×150 mL), benzene (2×100 mL), and then redissolved in ethanol (400 mL). The resulting solution was treated with propylene oxide (0.12 mole, 8.6 mL) at 25° C. for 30 minutes. The precipitate was collected by filtration, washed successively with ethanol and diethyl ether, and dried to give 6 g of α-amino-6,7-dichloro-3-(phosphonomethyl)-2-quinoxalinepropanoic acid. An analytical specimen was obtained after trituration with hot methanol and recrystallization from water-acetonitrile; m.p. 203° C. (dec); MS (neg. FAB) 378; $^1$H NMR (DMSO-d$_6$, 1 drop of DCl, 400 MHz): δ3.55 (m, 2H, CH$_2$—P), 3.82 (d, J=5.6 Hz, 2H, CH$_2$), 4.54 (t, J=5.6 Hz, 1H, CH), 8.29 and 8.32 (singlets, 2H, ArH).

Elemental analysis for C$_{12}$H$_{12}$Cl$_2$N$_3$O$_5$P: Calc'd: C, 37.92; H, 3.18; N, 11.03. Found: C, 37.61; H, 3.50; N, 10.76.

EXAMPLE 8

α-Amino-7-chloro-3-(phosphonomethyl)-2-quinoxalinepropanoic Acid

Following the procedure of Example 1, condensation of 1,4-dibromo-2,3-butanedione with 1,2-diamino-4-chlorobenzene yielded 2,3-bis(bromomethyl)-6-chloroquinoxaline, m.p. 149°-150° C.; $^1$H NMR (CDCl$_3$, 400 MHz): δ4.89 and 4.90 (singlets, 4H, CH$_2$), 7.74 (dd, J$_1$=8.9 Hz, J$_2$=2.3 Hz, 1H, H-7), 8.01 (d, J=8.9 Hz, 1H, H-8), 8.07 (d, J=2.3 Hz, 1H, H-5).

A mixture of 2,3-bis(bromomethyl)-6-chloroquinoxaline (0.176 mole, 60 g) and trimethyl phosphite (0.176 mole, 22 g) was refluxed in toluene (1200 mL) for 6 hours, the resulting solution was evaporated in vacuo, and the residue was subjected to a preparative HPLC using ethyl acetate-hexane. A homogenous fraction (12 g) of dimethyl 3-bromomethyl-6-chloroquinoxaline-2-methylphosphonate was separated, m.p. 159°-160° C.; $^1$H NMR (CDCl$_3$, 400 MHz): δ3.77 and 3.80 (singlets, 6H, CH$_3$O), 3.84 (d, J=22.4 Hz, 2H, CH$_2$—P), 4.95 (s, 2H, CH$_2$), 7.69 (dd, J$_1$=8.9 Hz, J$_2$=2.3 Hz, 1H, H-7), 7.98 (d, J=8.9 Hz, 1H, H-8), 8.42 (d, J=2.3 Hz, 1H, H-5). The structure was confirmed by single-crystal X-ray analysis. The isomeric dimethyl 3-bromomethyl-7-chloroquinoxaline-2-methylphosphonate was also collected (14 g, m.p. 129°-130° C.) and identified.

Using the procedure of Example 7, the intermediate 6-chloro substituted dimethyl phosphonate was converted into acetylamino-[7-chloro-3-[(dimethoxyphosphinyl)methyl]quinoxalin-2-yl]methyl-propanedioic acid diethyl ester; $^1$H NMR (DMSO-d$_6$, 400 MHz): δ1.15 (narrowly overlapping triplets, J=7.8 Hz, 6H, CH$_3$ of ethyl), 1.82 (s, 3H, CH$_3$CO), 3.64 (s, 3H, CH$_3$O), 3.72 (d, J=22.8 Hz, 2H, CH$_2$—P), 3.75 (s, 3H, CH$_3$O), 4.02 (br s, 2H, CH$_2$), 4.25 (m, 4H, CH$_2$ of ethyl), 7.84 (dd, J$_1$=8.9 Hz, J$_2$=2.2 Hz, 1H, H-6), 7.96 (d, J=2.2 Hz, 1H, H-8), 8.06 (d, J=8.9 Hz, 1H, H-5).

Hydrolysis of the product of the preceding paragraph was effected by hot 6N hydrochloric acid, as described in Example 7. The resultant α-amino-7-chloro-3-(phosphonomethyl)-2-quinoxalinepropanoic acid was obtained in a high yield; m.p. 181°-192° C.; $^1$H NMR (DMSO-d$_6$, 1 drop of DCl, 400 MHz): δ3.56 (m, 2H, CH$_2$—P), 3.81 (d, J=6 Hz, 2H, CH$_2$), 4.54 (t, J=6 Hz, 1H, CH), 7.82 (dd, J$_1$=8.9 Hz, J$_2$=2.3 Hz, 1H, H-6), 8.03 (d, J=8.9 Hz, 1H, H-5), 8.07 (d, J=2.3 Hz, 1H, H-8). Despite drying at 80° C. at 1 mm Hg over P$_2$O$_5$, this material contained residual solvents.

Elemental analysis for C$_{12}$H$_{13}$ClN$_3$O$_5$P.½H$_2$O.¼C$_2$H$_5$OH: Calc'd: C, 40.99; H, 4.27; N, 11.47. Found: C, 41.29; H, 4.66; N, 11.21.

EXAMPLE 9

α-Amino-5,8-dichloro-3-(phosphonomethyl)-2-quinoxalinepropanoic Acid 2,3-Bis(bromomethyl)-5,8-dichloro-quinoxaline, m.p. 155°-158° C.; $^1$H NMR (CDCl$_3$, 200 MHz): δ5.02 (s, 4H, CH$_2$), 7.82 (s, 2H, ArH) is reacted with trimethyl phosphite to obtain 3-bromomethyl-5,8-dichloro-quinoxaline-2-methylphosphonate, m.p. 140°-144° C.; $^1$H NMR (CDCl$_3$, 200 MHz): δ3.8 and 3.9 (singlets, 6H, CH$_3$O), 3.97 (d, J=22.7 Hz, 2H, CH$_2$—P), 5.02 (s, 2H, CH$_2$), 7.7 (s, 2H, ArH), which is reacted with diethyl acetamidomalonate to obtain acetylamino[5,8-dichloro-3-[(dimethoxyphosphinyl)methyl]quinoxalin-2-yl]methylpropanedioic acid diethyl ester, m.p. 74°-78° C.; $^1$H NMR (CDCl$_3$, 200 MHz): δ1.21 (t, J=8 Hz, 6H, CH$_3$ of ethyl), 1.89 (s, 3H, CH$_3$CO), 3.68 (d, J=22.8 Hz, 2H, CH$_2$—P), 3.80 and 3.86 (singlets, 6H, CH$_3$O), 4.2-4.35 (overlapping signals, 6H, CH$_2$), 7.16 (s, 1H, NH), 7.7 (s, 2H, ArH), which was directly hydrolyzed with 6N HCl to α-amino-5,8-dichloro-3-(phosphonomethyl)-2-quinoxalinepropanoic acid; m.p. 193° C. (dec); MS (neg. FAB) 378; $^1$H NMR (DMSO-d$_6$, 1 drop of DCl, 400 MHz): δ3.68 (doublet with additional splitting pattern, J=22 Hz, 2H, CH$_2$—P), 3.88 (d, J=5.8 Hz, 2H, CH$_2$), 4.62 (t, J=5.8 Hz, 1H, CH), 7.96 and 7.97 (singlets, 2H, ArH).

Elemental analysis for C$_{12}$H$_{12}$Cl$_2$N$_3$O$_5$P.0.5H$_2$O: Calc'd: C, 37.04; H, 3.36; N, 10.80. Found: C, 37.43; H, 3.31; N, 10.47.

EXAMPLE 10

α-Amino-6,7-difluoro-3-(phosphonomethyl)-2-quinoxalinepropanoic Acid

The title compound is prepared from 2,3-bis(bromomethyl)-6,7-difluoro-quinoxaline, m.p. 144°-145° C.; $^1$H NMR (DMSO-d$_6$, 400 MHz): δ5.02 (s, 4H, CH$_2$), 8.21 (t, J=9.7 Hz, 2H, ArH), by reaction with trimethyl phosphite to obtain 3-bromomethyl-6,7-difluoro-quinoxaline-2-methylphosphonate as an oil; $^1$H NMR (DMSO-d$_6$, 400 MHz): δ3.69 and 3.72 (singlets, 6H, CH$_3$O), 3.87 (d, J=11 Hz, 2H, CH$_2$—P), 5.04 (S, 2H, CH$_2$), 8.17 (t, J=10 Hz, 2H, ArH), which is reacted with diethyl acetamidomalonate and immediately subjected to direct hydrolysis with 6N HCl to yield α-amino-6,7-difluoro-3-(phosphonomethyl)-2-quinoxalinepropanoic acid; m.p. 208° C.; MS (neg. FAB) 346; $^1$H NMR (DMSO-d$_6$, 1 drop of DCl, 400 MHz): δ3.55 and 3.77 (m, 4H, CH$_2$), 8.02 (m, 2H, ArH).

Elemental analysis for C$_{12}$H$_{12}$F$_2$N$_3$O$_5$P.H$_2$O: Calc'd: C, 39.46; H, 3.86; N, 11.51. Found: C, 39.13; H, 3.74; N, 11.20.

EXAMPLE 11

α-Amino-6,7-dimethoxy-3-(phosphonomethyl)-2-quinoxalinepropanoic Acid

Following the same reaction sequence as in Example 10, 2,3-bis(bromomethyl)-6,7-dimethoxy-quinoxaline, m.p. 182°-183° C.; $^1$H NMR (CDCl$_3$, 200 MHz): δ4.06 (s, 6H, CH$_3$O), 4.88 (s, 4H, CH$_2$), 7.34 (s, 2H, ArH) is converted to 3-(bromomethyl)-6,7-dimethoxy-quinoxaline-2-methylphosphonate, m.p. 119°-122° C.; $^1$H NMR (CDCl$_3$, 200 MHz): δ3.73 and 3.85 (overlapping signals, 6H+2H, CH$_3$OP and CH$_2$—P), 4.07 (s, 6H, CH$_3$O), 4.96 (s, 2H, CH$_2$), 7.34 (broad s, 2H, ArH) and ultimately the title compound is obtained, m.p. 220° C. (dec); MS (neg. FAB) 370; $^1$H NMR (DMSO-d$_6$, 1 drop of DCl, 400 MHz): δ3.56 (m, 2H, CH$_2$—P), 3.69 (d, J=6 Hz, 2H, CH$_2$), 3.92 (broad s, 6H, CH$_3$O), 4.51 (t, J=6 Hz, 1H, CH), 7.37 and 7.39 (singlets, 2H, ArH).

Elemental analysis for C$_{14}$H$_{18}$N$_3$O$_7$P.H$_2$O: Calc'd: C, 43.19; H, 5.18; N, 10.79. Found: C, 43.39; H, 5.36; N, 10.71.

The compounds of this invention were established to be NMDA competitive antagonists by demonstrating their ability to displace tritiated 3-(2-carboxypiperazinyl-4-yl)propyl-1-phosphonic acid (CPP), which is a known competitive NMDA antagonist, in rat frontal cortex homogenates according to the procedure of Murphy et al., J. Pharmacol. Exp. Therap.: 240 (3) 778-784 (1987). Representative compounds of this invention completely inhibit [$^3$H] CPP binding at 10 μM concentrations. The IC$_{50}$ calculated for these compounds is as follows:

TABLE 1

| Compound | IC$_{50}$, nM |
| --- | --- |
| L-glutamic acid | 64 |
| D(−)-2-amino-5-phosphono-heptanoic acid | 639 |
| Example 1 | 110 |
| Laevoisomer of Example 3 | 29 |
| Example 4 | 22 |
| Example 5 | 6 |
| Example 7 | 4 |
| Example 8 | 24 |
| Example 10 | 166 |
| Example 11 | 832 |

In addition, representative compounds of the invention were shown to antagonize NMDA in vivo using essentially the procedure of Leander et al., Brain Res. 448 115 (1988). Male Swiss-albino mice (CD-1 strain, Charles River) 18-22 grams in weight, after 18 hours of food deprivation, were habituated to an observation chamber for 30 minutes. The mice were pretreated with the representative test compound followed thirty minutes later with NMDA, 195 mg/kg, i.p., which is a dose normally causing 90% mortality resulting from motor seizures including uncontrollable hind leg scratching or limbs and/or torso muscle jerking with loss of righting reflex followed by death within the 30 minute observation period after NMDA administration. From the latter, the $ED_{50}$ for survival is determined. The $ED_{50}$ values of less active congeners of this series were in the range of 20-100 mg/kg i.p. while several compounds displayed $ED_{50}$ at 1-10 mg/kg i.p. Compounds having activity in this test procedure are generally recognized in the scientific literature as having broad anti-convulsant utility. Representative data obtained in the NMDA-lethality model are presented in Table 2.

TABLE 2

| Compound | $ED_{50}$ mg/kg i.p. |
|---|---|
| Example 1 | 3.72 |
| Laevoisomer of Example 3 | 1.52 |
| Example 5 | 5.30 |
| Example 7 | 1.58 |
| Example 8 | 1.13 |

Therefore, the compounds of this invention are competitive NMDA antagonists useful in the treatment of convulsions, cerebral ischemias, stroke, brain or spinal cord injury, CNS disorders such as senile dementia, Alzheimer's disease, Huntington's chorea, and other dominant or recessive spinocerebellar degenerations. The said compounds may be especially useful as pre-anesthetics and neuroprotective agents during a high risk surgery, such as brain surgery and spinal cord surgery or as a result of trauma, where the risk of cardiac or pulmonary arrest may cause partial, temporary or complete loss of blood flow to the brain. Additional advantages in the use of the compounds of this invention as pre-anesthetics resides in their mild anxiolytic/sedative properties, their short term memory impairment property (short-term amnesia) and in their ability to potentiate the affect of anesthetics so that the latter may be employed at a lower dose.

Hence, there is herewith provided in addition to the novel compounds, supra, a method for preventing disorders induced by overstimulation of excitatory amino acid receptors in brain and spinal cord which comprises administering to a mammal suffering from such disease states, an NMDA antagonist of the formula presented, supra.

As such, the compounds of this invention may be administered neat or with a pharmaceutical carrier to a patient in need thereof. The pharmaceutical carrier may be solid or liquid.

A solid carrier can include one or more substances which may also act as flavoring agents, lubricants solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compounds can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

To determine the effective amount of the compounds to be administered in alleviation of CNS degenerative dysfunctions, the physician need only evaluate the effects of a given NMDA antagonist in the patient by incrementally increasing the oral dosage from about 1 mg/kg to about 20 mg/kg until the desired symptomatic relief level is achieved. The continuing dose regimen may then be modified to achieve the desired result, with the range of about 1 to 100 mg/day. Similar techniques are followed by determining the effective dose range upon i.v. or i.m. administration. When using the compounds prophylactically to arrest declining cognitive function as in Alzheimer's dementia, a more subjective approach is taken such as by relating the drug dosage to improved memory responses or analogous desired responses which can be related to relief of overstimulation of the excitatory amino acid receptors.

What is claimed is:

1. A compound of the formula:

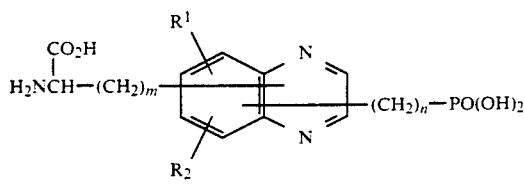

in which
the amino acid and phosphonic acid bearing groups are ortho to each other in the 2-, 3- or 6-, 7-positions of the quinoxaline nucleus and, when the acid bearing groups are in the 2-, 3-positions, $R^1$ and $R^2$ are, independently, hydrogen, alkyl of 1 to 6 carbon atoms, alkoxy of 1 to 6 carbon atoms, or halo, or taken together, $R^1$ and $R^2$ are butadienylene, otherwise $R^1$ and $R^2$ are hydrogen;
m is one of the integers 0, 1 or 2;
n is one of the integers 1, 2 or 3;
or a pharmaceutically acceptable salt, alkyl ester, in which the alkyl group has from 1 to 6 carbon atoms, or a

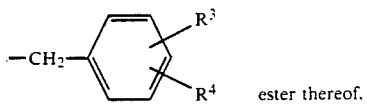 ester thereof.

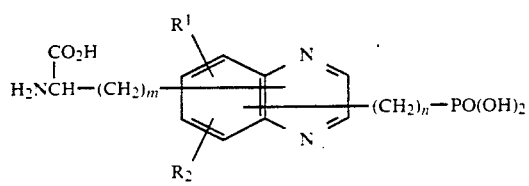

where
$R^3$ and $R^4$ are, independently, hydrogen, nitro, halo or methoxy.

2. A compound of the formula:

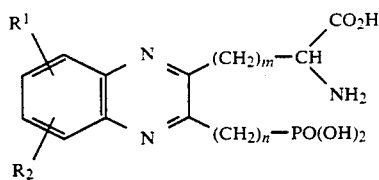

in which
$R^1$ and $R^2$ are, independently, hydrogen, alkyl of 1 to 6 carbon atoms, alkoxy of 1 to 6 carbon atoms, or halo, or taken together, $R^1$ and $R^2$ are butadienylene;
or a pharmaceutically acceptable salt, alkyl ester, in which the alkyl group has 1 to 6 carbon atoms, or benzyl ester thereof.

3. A compound of claim 2 in which the alkyl substituent is of 1 to 4 carbon atoms; the alkoxy substituent is of 1 to 6 carbon atoms; halo is chlorine, bromine or fluorine; m is 1; n is 1 or a pharmaceutically acceptable salt, alkyl ester in which the alkyl group has from 1 to 6 carbon atoms or benzyl ester thereof.

4. The compound of claim 1 which is α-amino-3-(phosphonomethyl)-2-quinoxalinepropanoic acid or a pharmaceutically acceptable salt, alkyl ester in which the alkyl group has from 1 to 6 carbon atoms or benzyl ester thereof.

5. The compound of claim 1 which is (−) α-amino-3-(phosphonomethyl)-2-quinoxalinepropanoic acid or a pharmaceutically acceptable salt, alkyl ester in which the alkyl group has from 1 to 6 carbon atoms or benzyl ester thereof.

6. The compound of claim 1 which is α-amino-6,7-dimethyl-3-(phosphonomethyl)-2-quinoxalinepropanoic acid or a pharmaceutically acceptable salt, alkyl ester in which the alkyl group has from 1 to 6 carbon atoms or benzyl ester thereof.

7. The compound of claim 1 which is α-amino-3-(phosphonomethyl)-2-benzo[g]quinoxalinepropanoic acid or a pharmaceutically acceptable salt, alkyl ester in which the alkyl group has from 1 to 6 carbon atoms or benzyl ester thereof.

8. The compound of claim 1 which is α-amino-6,7-dichloro-3-(phosphonomethyl)-2-quinoxalinepropanoic acid or a pharmaceutically acceptable salt, alkyl ester in which the alkyl group has from 1 to 6 carbon atoms or benzyl ester thereof.

9. The compound of claim 1 which is α-amino-7-chloro-3-(phosphonomethyl)-2-quinoxalinepropanoic acid or a pharmaceutically acceptable salt, alkyl ester in which the alkyl group has from 1 to 6 carbon atoms or benzyl ester thereof.

10. The compound of claim 1 which is α-amino-5,8-dichloro-3-(phosphonomethyl)-2-quinoxalinepropanoic acid or a pharmaceutically acceptable salt, alkyl ester in which the alkyl group has from 1 to 6 carbon atoms or benzyl ester thereof.

11. The compound of claim 1 which is α-amino-6,7-difluoro-3-(phosphonomethyl)-2-quinoxalinepropanoic acid or a pharmaceutically acceptable salt, alkyl ester in which the alkyl group has from 1 to 6 carbon atoms or benzyl ester thereof.

12. The compound of claim 1 which is α-amino-6,7-dimethoxy-3-(phosphonomethyl)-2-quinoxalinepropanoic acid or a pharmaceutically acceptable salt, alkyl ester in which the alkyl group has from 1 to 6 carbon atoms or benzyl ester thereof.

13. The compound which is α-amino-7-(phosphonomethyl)-6-quinoxalinepropanoic acid or a pharmaceutically acceptable salt, alkyl ester in which the alkyl group has from 1 to 6 carbon atoms or benzyl ester thereof.

14. A process for the treatment of cerebral ischemia which comprises administering to a mammal suffering from such disorder, a neuroprotective amount of an NMDA antagonist of the formula:

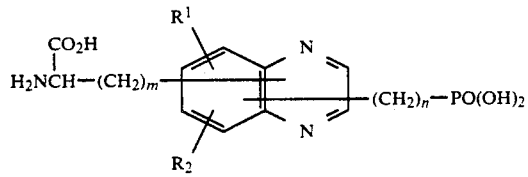

in which
the amino acid and phosphonic acid bearing groups are ortho to each other in the 2-, 3- or 6-, 7-positions of the quinoxaline nucleus and, when the acid bearing groups are in the 2-, 3-positions, $R^1$ and $R^2$ are, independently, hydrogen, alkyl of 1 to 6 carbon atoms, alkoxy of 1 to 6 carbon atoms, or halo, or taken together, $R^1$ and $R^2$ are butadienylene, otherwise $R^1$ and $R^2$ are hydrogen;

m is one of the integers 0, 1 or 2;

n is one of the integers 1, 2 or 3;

or a pharmaceutically acceptable salt, alkyl ester, in which the alkyl group has from 1 to 6 carbon atoms, or a

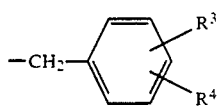 ester thereof.

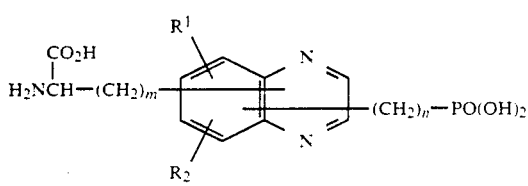

where $R^3$ and $R^4$ are, independently, hydrogen, nitro, halo or methoxy.

15. A pharmaceutical composition for the treatment of cerebral ischemia which comprises a compound of the formula:

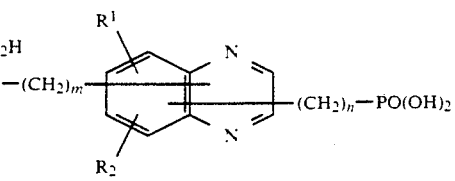

in which
the amino acid and phosphonic acid bearing groups are ortho to each other in the 2-, 3- or 6-, 7-positions of the quinoxaline nucleus and, when the acid bearing groups are in the 2-, 3-positions, $R^1$ and $R^2$ are, independently, hydrogen, alkyl of 1 to 6 carbon atoms, alkoxy of 1 to 6 carbon atoms, or halo, or taken together, $R^1$ and $R^2$ are butadienylene, otherwise $R^1$ and $R^2$ are hydrogen;
m is one of the integers 0, 1 or 2;
n is one of the integers 1, 2 or 3;
or a pharmaceutically acceptable salt, alkyl ester, in which the alkyl group has from 1 to 6 carbon atoms, or a

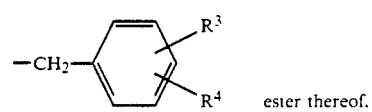 ester thereof.

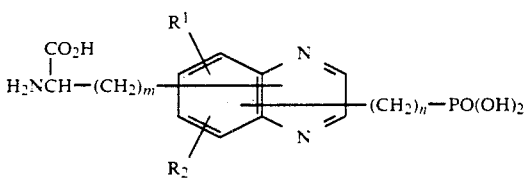

where
$R^3$ and $R^4$ are, independently, hydrogen, nitro, halo or methoxy;
and a pharmaceutically acceptable carrier therefor.

* * * * *

UNITED STATES PATENT AND TRADEMARK OFFICE
CERTIFICATE OF CORRECTION

PATENT NO. : 5,118,675

DATED : Jun. 2, 1992

INVENTORS : Ivo L. Jirkovsky, Reinhardt B. Baudy and Lynne P. Greenblatt

It is certified that error appears in the above -- identified patent and that said Letters Patent is hereby corrected as shown below:

Col. 13, line 35; Col. 15, line 29 and Col. 16, line 35, delete---

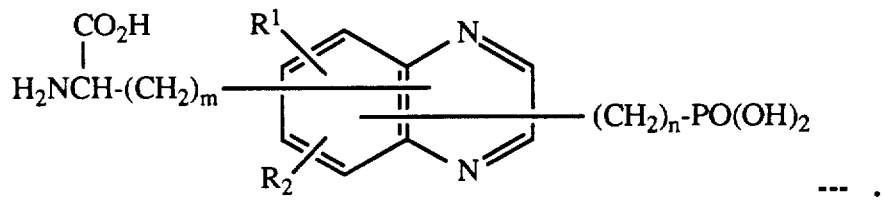

--- .

Signed and Sealed this

Thirty-first Day of August, 1993

*Attest:*

BRUCE LEHMAN

*Attesting Officer*  *Commissioner of Patents and Trademarks*